United States Patent [19]

Cordon et al.

[11] 4,174,387

[45] Nov. 13, 1979

[54] REDUCTION OF ABRASIVENESS IN DENTIFRICES

[75] Inventors: Martin Cordon, Highland Park; Robert E. Dickson, Belle Mead, both of N.J.

[73] Assignee: Colgate-Palmolive Company, New York, N.Y.

[21] Appl. No.: 764,131

[22] Filed: Jan. 31, 1977

Related U.S. Application Data

[63] Continuation-in-part of Ser. No. 544,618, Jan. 28, 1975, abandoned.

[51] Int. Cl.$^2$ .............................................. A61K 7/18
[52] U.S. Cl. ........................................ 424/52; 424/49
[58] Field of Search ................................... 424/49–58

[56] References Cited

U.S. PATENT DOCUMENTS

| | | | |
|---|---|---|---|
| 3,003,919 | 10/1961 | Broge | 424/49 |
| 3,060,098 | 10/1962 | Gershon | 424/52 |
| 3,105,013 | 9/1963 | Saul et al. | 424/52 |
| 3,670,076 | 6/1972 | Muhlor | 424/49 |
| 3,804,946 | 4/1974 | Harrison et al. | 424/52 |
| 3,906,090 | 9/1975 | Colodney | 424/52 |
| 3,911,104 | 10/1975 | Harrison | 424/52 |
| 3,937,804 | 2/1976 | Delaney et al. | 424/52 |
| 3,939,262 | 2/1976 | Kim | 424/52 |
| 4,020,154 | 4/1977 | Perla et al. | 424/52 |
| 4,036,949 | 7/1977 | Colodney | 424/52 |

*Primary Examiner*—Shep K. Rose
*Attorney, Agent, or Firm*—Robert L. Stone; Murray M. Grill; Herbert S. Sylvester

[57] ABSTRACT

Dentifrice possessing superior cleaning and polishing characteristics comprising a silicious and calcined alumina abrasive system in an amount to provide an enamel abrasion to the dentifrice of above about 450, (as measured by the radioactive method) and about 0.005–1.0% and preferably about 0.1–1.0% by weight of a water soluble fluoride salt, such as sodium fluoride, sodium monofluorophosphate, stannous fluoride and the like, with or without raising the pH of said composition to preferably above about 7 so as to reduce said enamel abrasion thereof.

6 Claims, No Drawings

REDUCTION OF ABRASIVENESS IN DENTIFRICES

This application is a continuation in part of copending patent application Ser. No. 544,618, filed Jan. 28, 1975, now abandoned.

This invention relates to a dentifrice having superior cleaning and polishing characteristics containing a relatively abrasive oral cleaning agent, ie. a hydrated silicious abrasive and a calcined alumina abrasive having a particle size of about 1 to 15 microns in diameter and in an amount to provide a radioactive enamel abrasion value (REA) above about 450 to the dentifrice; said calcined alumina being preferably present in an amount of at least about 7.5% and said silicious abrasive being present in amounts of at least 10% by weight of said dentifrice; and small amounts of a water-soluble fluoride salt capable of providing a soluble fluorine content of at least about 0.1%, to reduce the enamel abrasion of said composition, which may be further reduced by raising the pH of said dentifrice.

It has been difficult heretofore to provide dentifrices for use in the daily brushing and cleaning of teeth which provide a desirable balance of cleaning and polishing actions. This has been largely due to the difficulty in selecting suitable abrasives which will afford maximum removal of difficult stains and debris without damaging the enamel surfaces of the teeth.

The function of an abrasive substance in formulations intended for use in the oral cavity is to remove various deposits, including pellicle film from the surface of the teeth. Pellicle film is a tightly adherent film which often contains brown or yellow pigments and imparts an unsightly appearance to the teeth. An advantageous abrasive material for incorporation into dental formulations should maximize film removal without causing undue abrasion to the hard tooth tissues. The typical soft abrasive used in dental compositions, such as dicalcium phosphate and calcium pyrophosphate, although not unduly abrasive to tooth tissue, are not as effective as the hard abrasives in removing these undesirable deposits from the teeth. However, hard abrasives can present serious problems when present in dental preparations since their outstanding abrasive characteristics may cause undue abrasion to the oral hard tissues (enamel, dentin and cementum).

It has now been found that the addition of about 0.1-1.0% by weight of a water-soluble fluoride salt to a dental abrasive system comprising hydrated silicious abrasive and the hard abrasive calcined alumina, with or without raising the pH of said dentifrice above about 7, effects a substantial reduction in the enamel abrasion thereof. This is a particularly desirable feature when applied to an abrasive system containing the hard abrasive calcined alumina. Dentifrice formulations can now be made containing hard abrasives (heretofore relatively undesirable because of a tendency to abrade tooth enamel) to give superior polishing and cleaning without encountering the problem of excess enamel abrasion. In addition to reduced REA (radioactive enamel abrasion) values, there were other beneficial changes observed on highly polished human enamel surfaces brushed with these dentifrices; namely less grooving or scratching was seen under the microscope.

Accordingly, a dentifrice possessing superior cleaning and polishing action without increasing the enamel abrasivity thereof can be formulated comprising a silicious abrasive and calcined alumina abrasive having a particle size of about 1 to 15 microns in diameter and in an amount to provide a radioactive enamel abrasion to the dentifrice of above about 450 and an effective amount of a water-soluble fluoride salt to reduce the enamel abrasion of the dentifrice.

It has also been found that the enamel abrasion, as evidenced by REA values, is also reduced by increasing the pH of a dentifrice as shown by the following table, wherein the pH of a composition comprising 24% silicious abrasive and 10% alumina abrasive was modified by the addition of HCl and NaOH.

TABLE I

| pH | additive | REA | RDA* |
|---|---|---|---|
| 4 | HCl | 4855 | 714 |
| 5 | HCl | 2563 | 432 |
| 6 | HCl | 1200 | 338 |
| 6.6 | unadjusted | 891 | 353 |
| 7 | NaOH | 792 | 342 |
| 8 | NaOH | 656 | 348 |
| 9 | NaOH | 488 | 349 |
| 10 | NaOH | 434 | 346 |

*Radioactive Dentin Abrasion Value

This table clearly shows that the enamel abrasivity is sensitive to pH in the 5-10 range, with the abrasivity decreasing as the pH increases; whereas the dentin abrasivity remains substantially the same within the pH range of 6-10.

The effectiveness of reducing the enamel abrasivity by modifying the pH of a dentifrice containing a silicious abrasive and calcined alumina with and without 0.22% NaF is clearly shown in the following table, wherein the abrasive constituted 10% calcined alumina and 24% silicious abrasive.

TABLE II

| | REA | | RDA | |
|---|---|---|---|---|
| pH | none | 0.22% NaF | none | 0.22% NaF |
| 5 | 1374 | 1448 | 458 | 475 |
| 7 | 880 | 508 | 426 | 415 |
| 9 | 663 | 434 | 442 | 420 |

This table also shows the combined salt and pH effects on enamel abrasivity. The small increase in REA at pH 5 is non-significant. It is noted that the dentin abrasivity remains substantially unaffected.

The following table additionally shows the additive or combined effects of pH and the fluorides on the enamel abrasivity of a dentifrice comprising 24% hydrated silicious abrasive and 10% calcined alumina. The pH of the dental creams were unadjusted.

TABLE III

| | REA | | | |
|---|---|---|---|---|
| Salt | Test 1 | Test 2 | RDA | pH |
| None (Control) | 859 | 704 | 323 | 6.2 |
| 0.76% MFP* | 623 | 512 | 315 | 6.5 |
| 0.22% NaF | 209 | — | 296 | 7.2 |
| 0.005% NaF | — | 622 | — | 6.4 |
| 0.4% SnF$_2$ | 739 | — | 350 | 5.3 |
| 0.2% CaF$_2$ | 799 | — | 316 | 6.3 |

*MFP is/sodium monofluorophosphate a trademark for

This table shows that NaF is more effective than MFP at the same F level. However, when the amount of soluble F ion (0.005%) present in MFP was added to the composition, the reduction in REA is not as great as that caused by the MFP, thereby establishing an effect by MFP. The highly insoluble $CaF_2$ had little effect. At higher pH than 5.3, $SnF_2$ would probably give a larger reduction than indicated here. This table shows that in general, NaF is the most effective of the additives.

Accordingly, it is preferable to adjust the pH of the dentifrice so as to obtain a further reduction in the enamel abrasivity thereof. This may be effected by the addition of suitable alkaline buffering agents or by the very presence of the fluoride salt. pH adjustment can be obtained by the addition of appropriate amounts of sodium hydroxide, sodium hydrogen phosphate, trisodium phosphate, sodium bicarbonate, etc.. Particularly useful buffer systems include sodium carbonate-bicarbonate, tetrasodium pyrophosphate, and a phosphate buffer system comprising $Na_2HPO_4$ and $Na_3PO_4$, wherein there is selected the appropriate ratio of compounds to give the desired pH.

Hard, inorganic, mineral-like substances, well known for their abrasive properties, are not generally suitable per se as dentifrice cleaning agents because they are too abrasive. However, the hardness of a certain class of particulate mineral-like substances provide effective cleaning and polishing, while their abrasiveness is minimized by the addition of small amounts of a soluble fluoride salt. The addition of an alkaline buffer effects an additional reduction in enamel abrasivity of the dentifrice. The inorganic mineral-like substance should be capable of providing to a dentifrice an REA above about 450 units, when present in an amount of at least about 7.5% by weight of said dentifrice, and should be in particulate form with a mean particle diameter in the range of about 1 micron to 15 microns. The preferred particle size range is 1 to 10 microns. This hard dental abrasive substance is calcined alumina and is capable of providing an REA value above about 450 to a dentifrice. Most commercial dentifrices presently on the market have an REA value up to about 300, and as low as 50.

Calcined alumina is the preferred abrasive in this invention. Flaked calcined alumina is defined as flat flakes of alpha-alumina crystals, of disc- or plate-like configuration, said flakes having a mean (by weight) particle diameter of less than about 7 microns (e.g., about 2 to 7 microns). Viewed under a scanning electron microscope, the flat alumina particles have sharp edges indicating that they have been fractured perpendicular to their flat parallel faces. Generally, the thickness of the flat flakes are less than about ⅓ (e.g., about ⅓ to 1/10) of their diameters, and are in the range of about ½ micron (or less) to about 2 microns (e.g., about 1 micron). The flat alpha-alumina crystals (Microgrit) and a process for preparing them are described in U.s. Pat. No. 3,121,623.

Another calcined alumina abrasive useful herein is defined in copending patent application Ser. No. 675,098, filed Apr. 9, 1976, the disclosure of which is incorporated herein by reference, as crystals of alpha-alumina ground to its ultimate particle form and having a mean ultimate particle size of about 1 to 2 microns.

A calcined alumina product available commercially as RC-152 DBM is very dense and highly stable. It has a mean particle size between about 1 to 2 microns, typically about 1.6 microns. Its typical size distribution is as follows:

| Particle Diameter μ | Percent of Particles Finer than corresponding diameter |
|---|---|
| 10 | about 100 |
| 5 | about 95 |
| 3 | about 85 |
| 2 | about 75 |
| 1 | about 25 |
| 0.5 | about 5 |

Under an electron microscope the larger particles appear flat with sharp sides and the smaller irregularly rounded in circular and oval shapes.

Crystalline alumina RC-152 DBM is ground from a coarser alumina commercially available as RC-152. RC-152 has a crystal particle size such that 98% of the particles pass through a 200 mesh screen and 25% pass through a 100 mesh screen.

The crystalline alpha alumina has been observed to be chemically

|  | % by weight | ppm |
|---|---|---|
| $Al_2O_3$ | 99.7 | |
| $Na_2O$ | 0.04 | |
| $SiO_2$ | 0.065 | |
| $Fe_2O_3$ | 0.024 | |
| $TiO_2$ | 0.0016 | |
| MnO | 0.0012 | |
| CaO | 0.045 | |
| $Cr_2O_3$ | 0.00036 | |
| $B_2O_3$ | 0.001 | |
| $F_2$ | | 200 |
| alpha phase alumina | 90 | |

The proportion of the calcined alumina (flat alumina particles) in the dentifrice may be, for instance, above 7.5% and in the range of about 7.5 to 20%, preferably about 7.5 to 15%.

In addition to the calcined alumina abrasive, a sufficient amount of silicious abrasive as an additional dental abrasive is preferably included. Accordingly, the silicious abrasive is soft by comparison, and has been conventionally employed in toothpastes. The silicious abrasive particularly useful herein is an amorphous alkali metal or alkaline earth metal alumino-silicate having a refraction index of about 1.44–1.47, and containing at least about 70% silica, up to about 10% alumina, up to about 20% by weight of moisture and up to about 10% by weight of sodium oxide, the moisture content preferably being about 10–20% by weight, measured by loss at 1000° C. and the typical content of sodium oxide being about 5–10% by weight.

The silicious dental abrasive may have a particle size of about 2 to 40 microns and may also be present in the form of relatively large agglomerates (of the individual particles) of such size as to be visible to the naked eye but easily reduced to the fine impalpable particle size upon being subjected to tooth-brushing in the mouth. Such agglomerates may be agglomerated with or without binding agent which may be water-soluble or water-insoluble.

For most purposes it is preferable that the silicious dental abrasive have a particle size less than 20 microns to avoid any gritty feel.

The proportion of this additional silicious dental abrasive in the dentifrice is usually in the range of about 10 to 70% and preferably 10 to 50%, and is preferably such that when the alpha-alumina is omitted from the dentifrice, the RDA (radioactive dentin abrasion) is in the range of about 100 to 600, preferably about 100 or 200 to 450.

The use of small amounts of the fluoride salts in oral preparations for the care and hygiene of the oral cavity has heretofore been known. However, its use with certain abrasive systems as an effective means of reducing the abrasivity thereof while maintaining the superior polishing properties of the dentifrice has heretofore been unknown.

It has been found that the reduction in abrasivity is particularly effective in the hydrated silicious-calcined alumina abrasive system defined herein.

The fluoride salts found particularly effective in reducing the enamel abrasion of the silicious-calcined alumina abrasive system include the water-soluble fluoride salts such as sodium fluoride, sodium monofluorophosphate, and stannous fluoride, in amounts of about 0.005–1.0% and preferably 0.1–1.0% by weight of the total formulation.

To make toothpastes or dental creams, the hard abrasive such as the flat flakes of alpha-alumina and the silicious abrasive are dispersed in a dental vehicle which preferably contains a liquid which is water and/or a humectant such as glycerine, sorbitol, xylitol, propylene glycol or polyethylene glycol 400, including suitable mixtures thereof. It is usually advantageous to use a mixture of both water and one or two humectants. Polyethylene glycols of higher molecular weight, e.g., polyethylene glycol 600 etc., may also be present. The total liquid content is generally well over 20% by weight of the vehicle (sorbitol, generally present in admixture with water, is considered as a liquid for this purpose). The preferred humectants are glycerine and sorbitol. Typically, the vehicle contains about 0–80% by weight of glycerine, up to about 80% by weight of sorbitol and about 5–80% of water.

The fluoride salt may be added directly to the dental vehicle containing the abrasives, or the abrasives may be pretreated with an aqueous solution of said salt and the pretreated abrasives added to a suitable dental vehicle. The soluble fluoride salts are dissolved in an aqueous solution and stirred with the abrasives (both the hard and soft abrasive) for a period of time, such as about 5 minutes. The solids are then isolated and washed twice with water. The salt-treated abrasive is then incorporated into a dental vehicle. The reduction in enamel abrasiveness exhibited by the dentifrice containing the pretreated abrasives is less than the reduction effected by the direct addition of the fluoride to the dental vehicle containing the abrasives as evidenced by the following results. The pH of all the compositions were maintained at a pH of 7.

TABLE IV

| Abrasive | REA Additions | | |
|---|---|---|---|
| | none | 0.22% NaF | pretreated with NaF |
| 24% silicious abrasive 10% calcined alumina | 880 | 572 | 642 |
| 24% silicious abrasive | 255 | 141 | 226 |
| 10% calcined glumina | 681 | 427 | 563 |
| | RDA | | |
| 24% silicious abrasive 10% calcined alumina | 426 | 399 | 434 |
| 24% silicious abrasive | 289 | 273 | 316 |
| 10% calcined alumina | 280 | 222 | 244 |

This table illustrates the general effectiveness of the fluorides in reducing the enamel abrasivity of each of the abrasives separately as well as the combination thereof, whether by direct addition of the fluoride or by pretreating the abrasives therewith. However, in view of the greater reduction in abrasivity effected by the direct addition of the soluble fluoride to the abrasives, it is preferable to add said fluoride directly to the dental vehicle during the process of preparing a dentifrice.

The vehicle usually also contains a thickening or gelling agent, such as the natural and synthetic gums and gum-like materials, such as Irish Moss, gum tragacanth, alkali metal (e.g., Li, K or Na) carboxymethyl cellulose and hydroxymethyl carboxyethyl cellulose, polyvinyl pyrrolidone, starch, xylitol, water-soluble hydrophilic colloidal carboxyvinyl polymers such as those sold under the trademark Carbopol 934 and 940, hydroxyethyl cellulose, Indian gum, acacia gums, agar agar, locust bean gum, Laponite CP or SP, which are each synthetic inorganic complex silicate clays sold under trademark by Laporte Industries, Ltd., and pectin or inorganic thickeners such as colloidal silica, e.g., synthetic finely divided silicas including those sold under the trademarks Cab-O-Sil M5, Syloid 244, Syloid 266, Zeosyl 200 and Aerosil D200. The solid portion of the vehicle is typically present in an amount up to about 10% by weight of the toothpaste and preferably within the range of about 0.5–8% by weight.

Fine particles of thermoplastic resin may also be present, such as particles of solid polymer having a molecular weight above 1000 (and preferably above 10,000, e.g., about 10,000 to 100,000 or more) and a mean diameter less than about 50 microns (preferably in the range of about 0.5 to 50 microns, e.g., about 10 to 30 microns). The polymer particles may be prepared directly by emulsion or suspension polymerization or by grinding the polymer in bulk, and may be present in amount of up to about 60% or more of the dentifrice, e.g., in the range of about 20 to 60%, such as about 20 to 50%, e.g., about 30 to 50% in a toothpaste. Examples of thermoplastic resins are polymerized ethylenically unsaturated compounds, such as polyolefines (e.g., polyethylene or polypropylene) or vinyl or vinylidene resins, such as polyvinyl chloride, polystyrene, vinyl chloridevinyl acetate copolymers, styrene-butadiene copolymers, polyvinylidene chloride, polyamides such as Nylon (e.g., Nylon 6); cellulosics such as cellulose acetate, etc..

The toothpaste may also contain surface-active agent, e.g., to achieve increased prophylactic action, assist in achieving thorough and complete dispersion of the instant compositions throughout the oral cavity, and render the instant compositions more cosmetically acceptable. The organic surface-active material may be anionic, nonionic, ampholytic, or cationic in nature, and it is preferred to employ as the surface-active agent a detersive material which imparts to the composition detersive and foaming properties. Suitable types of such detergents are water-soluble salts of higher fatty acid monoglyceride monosulfates, such as sodium salt of the monosulfated monoglyceride or hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1,2 hydroxy propane sulfonates, and the substantially saturated higher aliphatic acyl amides of lower aliphatic amino carboxylic acid compounds, such as those having 12 to 16 carbons in the fatty acid alkyl or acyl radicals, and the like. Examples of the last-mentioned amides are N-lauroyl sarcosine, and the sodium, potassium, and ethanolamine salts of N-lauroyl, N-myristoyl or N-palmitoyl sarcosinates, which should be substantially free from soap or similar higher fatty acid material which tends to substantially reduce the effect of these compounds. The use of these sarcosinate compounds in dentifrice compositions of the present invention is particularly advantageous since these materials exhibit a prolonged and marked effect in the inhibition of acid in the oral cavity due to carbohydrates, in addition to exerting some reduction in the solubility of tooth enamel in acid solutions.

Other suitable surface-active materials include non-ionic agents such as condensates of sorbitan monostearate with approximately 60 moles of ethylene oxide, condensates of ethylene oxide with propylene oxide condensates of propylene glycol ("Pluronics") and cationic surface-active germicides and antibacterial compounds such as di-isobutylphenoxyethyldimethyl benzyl ammonium chloride, benzyl dimethyl stearyl ammonium chloride, tertiary amines having one fatty alkyl group (of from 12 to 18 carbon atoms) and two (poly) oxyethylene groups attached to the nitrogen (typically containing a total of from about 2 to 50 ethenoxy groups per molecule) and salts thereof with acids, and compounds of the structure:

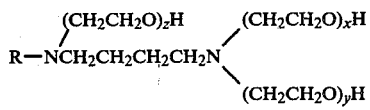

where R is a fatty alkyl group containing from about 12 to 18 carbon atoms, and x, y and z total 3 or higher, as well as salts thereof with mineral organic acids, may also be used. It is preferred that the total amount of surface-active agent be about 0.05-5% by weight, preferably about 1-3%, of the dentifrice.

Various other materials may be incorporated in the oral preparation of this invention. Examples thereof are coloring or whitening agents such as titanium dioxide, preservatives, silicones, chlorophyll compounds, ammoniated materials, such as urea, diammoniumphosphate and mixtures thereof, and other constituents. Each of these adjuvants may be typically incorporated in the instant toothpastes in amounts up to about 5%.

The toothpaste may also contain antibacterial agents in amounts of about 0.01-5%. Typical examples of such agents are guanidines, biguanides and amines such as:
  $N^1$-(4-chlorobenzyl)-$N^5$-2,4-(dichlorobenzyl)biguanide;
  p-chlorophenyl biguanide;
  4-chlorobenzhydryl biguanide;
  4-chlorobenzhydrylguanylurea;
  $N^1$-3-lauroxypropyl-$N^5$-p-chlorobenzylbiguanide;
  1,6-di-p-chlorophenylbiguanidohexane;
  1-(lauryldimethylammonium)-8-(p-chlorobenzyldimethylammonium) octane dichloride;
  5,6-dichloro-2-guanidinobenzimidazole;
  $N^1$-p-chlorophenyl-$N^5$-laurylbiguanide;
  5-amino-1, 3-bis (2-ethylhexyl)-5-methylhexahydropyrimidine; and their non-toxic acid addition salts;
  Benzethonium chloride
  Cetyl pyridinium chloride Suitable flavoring or sweetening sialagogues may be employed in formulating a flavor for the compositions of the present invention. Examples of suitable flavoring constituents include the flavoring oils, e.g., oils of spearmint, peppermint, wintergreen, sassafras, clove, sage, eucalyptus, marjoram, cinnamon, lemon and orange, as well as methyl salicylate. Suitable sweetening agents include sucrose, lactose, maltose, sorbitol, xylitol, sodium cyclamate and saccharin. Suitably, flavor and sweetening agent may together comprise from about 0.01 to 5% or more of the compositions of the instant invention.

The dentifrice may be prepared by suitably mixing the ingredients. For instance in making a toothpaste, a gelling agent such as sodium carboxymethyl cellulose or Carbopol 934 and a preservative such as sodium benzoate, if employed, is dispersed with a humectant such as glycerine. Water may also be present. Additional humectant and water, as an aqueous 70% sorbitol solution, may then be mixed with the dispersion and a paste, gel or cream is formed. Dental abrasive agent, surface-active agent and flavor are then added. The toothpaste is then thoroughly deaerated (e.g., in vacuo) and tubed.

Preferably the amount of water-insoluble essential flavoring oil is above 0.5% and below 2%. Strongly flavored toothpastes contain above 1% of such flavoring oil, e.g., about 1.2 to 1.5%.

Instant formulations have been found useful as prophylactic dental pastes applied professionally, preparations for use on dentures and for daily use on the teeth.

The following examples are given to illustrate this invention further. In this application all proportions are by weight unless otherwise indicated.

EXAMPLE 1

A toothpaste is prepared according to the following formulation: glycerine 25%; sodium carboxymethyl cellulose 1.4%; sodium benzoate 0.50%; sodium saccharin 0.20%; sodium aluminosilicate (silicious abrasive) 20.0%; titanium dioxide 0.4%; calcined alumina ("Microgrit") 8.0%; sodium lauryl sulfate 1.5%; flavoring oil 1.0%; deionized water q.s.

The sodium alumino-silicate (silicious abrasive) contains about 89-91% silica, about 0.8-1.2% alumina, about 1.3-0.9% sodium oxide and about 10% water (determined by loss on ignition at 1000° C.). This toothpaste has an REA value of 848, and an RDA value of 367. The alpha alumina flakes of the "Microgrit" alumina has a mean particle diameter of about 4 microns, all the particles thereof having diameters less than 10 microns, about 85-95% (by weight) have diameters less than 6.0 microns and about 30-35% have particle diameters less than 3.5 microns.

REA represents the radioactive enamel abrasion value obtained by a technique described in the literature.

A method for determining enamel abrasion values for the agents is as follows: Molar teeth are exposed to neutron radiation whereby a predetermined portion of phosphate content is converted to $P^{32}$. Each enamel specimen is mounted in a self-curing polymer such as methyl methacrylate. The specimens are then placed in the specially designed apparatus consisting essentially of a means of stabilizing the enamel specimen, a tube to contain the diluted toothpaste and a toothbrush head under a tension of 150 grams. The enamel specimen is then subjected to 4500 reciprocal brush strokes over the cusped surface. A 2.0 ml aliquot is placed in a planchet, dried at room temperature, and the radioactivity ($P^{32}$) determined using a conventional Geiger-Mueller detector. By comparing the radioactivity of the slurries of the experimental pastes to that obtained on each enamel specimen with a reference, calcium pyrophosphate powder which is arbitrarily assigned an enamel abrasion score of 500, the relative abrasiveness of the experimental pastes may be determined.

The RDA values may be suitably determined using the dentin portions separated from human cuspids and subjecting said dentin to 1000 reciprocal brush strokes. This radioactive technique is more fully described in the literature: Stookey, C. K. and Muhler, J. C., J. Dental Research 47 524–538 (1968). Similarly to the REA values, the dentin abrasion must likewise not be high in order to prevent or minimize oral hard tissue damage.

EXAMPLES 2 AND 3

Example 1 is repeated except that 0.76 MFP and 0.22% NaF is added respectively to the dental cream.

| Example 2 | Example 3 |
|---|---|
| MFP containing cream | NaF containing cream |
| REA: 509 | 370 |
| RDA: 371 | 335 |

The above results clearly indicate that the addition of a fluoride salt in amounts less than 1% effects a considerable reduction in the REA value, namely, from 848 of the control to 509 and 371 respectively, without substantially affecting the RDA values thereof.

EXAMPLES 4 AND 5

Examples 2 and 3 are repeated except that the calcined alumina content is changed to 5% "Microgrit" and 5% RC-152 DBM alumina flakes, another brand of calcined alumina aforedefined, and the sodium alumino-silicate content is increased to 24%.

|  | REA | RDA |
|---|---|---|
| Control | 858 | 267 |
| Example 6 (.22% NaF) | 483 | 232 |
| Example 7 (.76% MFP) | 795 | 239 |

A reduction in abrasivity is evidenced with the addition of the fluorides, a greater reduction occurring when NaF is the additive.

It is also within the broader scope of the invention to include other alpha aluminas in admixture with the amorphous silicious abrasive.

Suitable alkaline agents and alkaline buffering agents may be added to further modify the above examples, inclusive of sodium hydroxide, sodium hydrogen phosphate, trisodium phosphate, sodium carbonate-bicarbonate, tetrasodium pyrophosphate and $Na_2HPO_4$ and $Na_3PO_4$.

While the silicious and calcined alumina abrasives together with the fluoride salt have proved most useful thus far in toothpastes, they may also be similarly incorporated into toothpowders or into dental creams which are of pourable consistency.

The particle diameters given in the examples are determined by conventional methods. Thus, the standard liquid sedimentation technique may be used. The calculation of particle diameter from the sedimentation data being made (as is conventional) on the basis of Stokes' Law, disregarding the particular shape of the particles.

It is understood that the foregoing detailed description is given merely by way of illustration and that variations may be made therein without departing from the spirit of the invention. The "Abstract" given above is merely for the convenience of technical searchers and is not to be given any weight with respect to scope of the invention.

We claim:

1. A dentifrice having a pH above about 7 obtained by incorporation therein of not more than an effective amount of an alkaline buffering agent, and having cleaning and polishing characteristics containing the abrasive system consisting of at least 10 and up to 70% of an amorphous alkali metal or alkaline earth metal aluminosilicate and at least 7.5% and up to 20% of calcined alumina in the form of alpha-alumina flakes having a particle size of about 1 to 15 microns in diameter and in an amount to provide a radioactive enamel abrasion value to the dentifrice of above about 450, and about 0.005–1.0% of a water soluble fluoride salt to reduce the enamel abrasion of the dentifrice.

2. A dentifrice in accordance with claim 1, wherein the fluoride salt is sodium fluoride.

3. A dentifrice in accordance with claim 1, wherein the fluoride salt is sodium monofluorophosphate.

4. A dentifrice as in claim 1, in which the proportion of said alumino-silicate is in the range of about 10 to 50% and the proportion of said calcined alumina is about 7.5 to 20%.

5. A dentifrice as in claim 1, wherein said alumino-silicate is sodium alumino-silicate containing at least about 70% silica, up to 10% alumina, about 10–20% water and up to 10% sodium oxide.

6. A dentifrice as in claIm 1, wherein the abrasive system is pretreated with the water-soluble fluoride salt.

* * * * *